United States Patent [19]

Martin et al.

[11] 4,251,516
[45] Feb. 17, 1981

[54] 2-DEOXY-3-O-DEMETHYLFORTIMICINS

[75] Inventors: Jerry R. Martin; John S. Tadanier, both of Waukegan; Paulette Johnson, Zion, all of Ill.

[73] Assignee: Abbott Laboratories, North Chicago, Ill.

[21] Appl. No.: 79,132

[22] Filed: Sep. 26, 1979

[51] Int. Cl.³ .................. A61K 31/71; C07H 15/22
[52] U.S. Cl. .................... 424/180; 536/4; 536/17 R
[58] Field of Search ............ 536/17 R, 17 B; 424/180

[56] References Cited

U.S. PATENT DOCUMENTS

| 4,124,756 | 11/1978 | Martin et al. | 536/17 R |
| 4,169,198 | 9/1979 | Martin et al. | 536/17 R |

Primary Examiner—Johnnie R. Brown
Attorney, Agent, or Firm—Gildo E. Fato; Robert L. Niblack; Joyce R. Niblack

[57] ABSTRACT

The present invention provides 2-deoxy-3-O-demethylfortimcins A and B and the 4-N-acyl and alkyl derivatives thereof, represented by the formula:

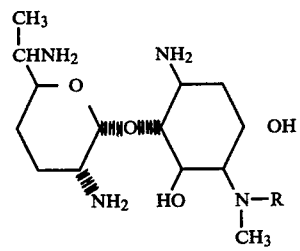

wherein R is selected from the group consisting of hydrogen, acyl, aminoacyl, diaminoacyl, N-monoloweralkylaminoalkyl, N,N-diloweralkylaminoalkyl, hydroxy-substituted aminoacyl, loweralkyl, aminoloweralkyl, N-monoloweralkylaminoloweralkyl, N,N-diloweralkylaminoloweralkyl and hydroxy-substituted aminoloweralkyl and the pharmaceutically acceptable salts thereof.

19 Claims, No Drawings

2-DEOXY-3-O-DEMETHYLFORTIMICINS

BACKGROUND OF THE INVENTION

Aminoglycoside antibiotics are a useful class of antibiotics which include the streptomicins, kanamycins, neomycins, gentamicins, tobramycins, amikacin, and the more recently discovered fortimicins. It is known that the antibacterial and pharmacological properties of many of the naturally produced aminoglycoside antibiotics can be advantageously altered by structural modifications. For example, certain chemical modifications in the gentamicin and kanamycin family of antibiotics provide compounds which are either less toxic than the parent antibiotic or are intrinsicly more active either by virtue of an altered antibiotic spectum of by virtue of an increased activity against resistant strains or an increase in the basic acitivy of the naturally produced antibiotic.

Chemical modification has also been found to be of value in the fortimicin family of antibiotics. Modifications producing the most active derivatives of fortimicin A are the modifications providing the 2-deoxyfortimicins disclosed in commonly assigned U.S. Pat. Nos. 4,192,867 and 4,187,297 and the 3-O-demthylfortimicins disclosed in U.S. Pat. No. 4,124,756, issued Nov. 7, 1978.

While highly active fortimicin derivatives have already been provided, because of the resistance problem rapidly encountered with aminoglycoside therapy, there is a need for improved entities or entities which exhibit comparable antibacterial spectra but which can be held in reserve in the event that current therapy becomes of less value because of the development of resistant organisms. The present invention provides one class of fortimicins which fullfill the above need.

SUMMARY OF THE INVENTION

The present invention provides 2-deoxy-3-O-demethylfortimcins A and B and the 4-N-acyl and alkyl derivatives thereof, represented by the formula:

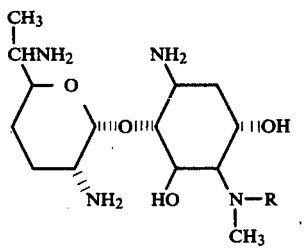

wherein R is selected from the group consisting of hydrogen, acyl, aminoacyl, diaminoacyl, N-monoloweralkylaminoalkyl, N,N-diloweralkylaminoalkyl, hydroxy-substituted aminoacyl, loweralkyl, aminoloweralkyl, N-monoloweralkylaminoloweralkyl, N,N-diloweralkylaminoloweralkyl and hydroxy-substituted aminoloweralkyl and the pharmaceutically acceptable salts thereof.

The compounds of this invention are useful as broad spectrum antibiotics, and surprisingly have been shown to be more active against certain strains of microorganisms susceptible to fortimicin therapy than either fortimicin A, 2-deoxyfortimicin A or 3-O-demethylfortimicin A, thought to be, of the fortimicins investigated to date by applicants, the most potent of the fortimicins.

DETAILED DESCRIPTION OF PREFERRED EMBODIMENTS

The fortimicin antibiotics of this invention are 2-deoxy-3-O-demethyl derivatives of fortimicins A and B and of 4-N-fortimicin B derivatives represented by formula I supra.

The term "loweralkyl," as used herein, refers to straight and branched chain alkyl radicals having from 1 to 6 carbon atoms and includes, but is not limited to methyl, ethyl, n-propyl, iso-propyl, n-butyl, iso-butyl, tert-butyl, n-pentyl, 1-methylbutyl, 2,2-dimethylpropyl, n-hexyl, 2-methylpentyl and the like.

The term "acyl," as used in the definitions of R in formula I, refers to acyl radicals of loweralkylcarbocyclic acids represented by the formula

wherein R is loweralkyl, i.e. acetyl, propionyl, butyryl, valeryl, etc.

The terms aminoacyl, hydroxy-substituted aminoacyl, etc. include, but are not limited to the naturally occurring amino acids residues such as glycyl, valyl, alanyl, sarcosyl, leucyl, isoleucyl, prolyl, seryl, histidyl and like amino acid residues as well as groups such as 2-hydroxy-4-aminobutyryl and the like. The amino acid residues included in such terms can, with the exception of glycine which has no center of symmetry, be either in the D or L configurations, or mixtures thereof, and are in the L configuration unless otherwise specified.

The term "pharmaceutically acceptable salts" refers to the non-toxic acid addition salts of the compounds of formula I which can be prepared either in situ during the final isolation or by reacting the free base with a suitable organic or inorganic acid by methods well known in the art. Representative salts include the mono-, di-, tri-, tetra- or other pre-salts such as the hydrochloride, hydrobromide, sulfate, bisulfate, acetate, oxalate, valerate, oleate, palmitate, stearate, laurate, borate, benzoate, lactate, phosphate, tosylate, citrate, maleate, fumarate, succinate, tartrate, napsylate and like salts.

The compounds of this invention are effective antibacterial agents against susceptible or sensitive strains of gram negative and gram positive microorganisms such as Staphylococcus aureus, Enterobacter aerogenes, Escherichia coli, Klebsiella pneumoniae, Providencia, Psuedomonas aeruginosa, Salmonella typhimurium, Serratia marcescens Shigella sonnei, Proteus vulgaris and Proteus mirabilis. While it is preferred to administer the compounds parenterally, generally in divided dosages of from one to 100 mg/kg of body weight daily, preferrably from about 2 to about 20 mg/kg daily, based on lean body weight, the compounds can be administered orally to sterilize the intestinal tract and can also be administered in suppository form.

The term "sensitive or susceptible strains" refers to strains of bacilli or organisms which have been demonstrated to be sensitive to a particular antibiotic in a standard in vitro sensitivity test and thus in vitro activity has been established for a particular antibiotic against a specific strain or strains of one or more organisms.

The compounds of this invention can be prepared according to the following general procedure. 2-deoxyfortimicin A, 2-deoxyfortimicin B or any other appropriate 2-deoxyfortimicin B derivative is O-demethylated by reacting the 2-deoxyfortamine-containing moiety with boron trihalide in a suitable solvent such as methylene chloride. The reactants are admixed in the solvent and the reaction is allowed to proceed at a suitable temperature for the desired period. The resulting 2-deoxy-3-O-demethylfortimicin is isolated by conventional column chromatography. Alternatively, the 2-deoxy-3-O-demethylfortimicin may be isolated by treating the crude reaction mixture, after passage through an anion exchange resin sufficient to remove bromide ion, with an appropriate N-protecting reagent such as N-(benzyloxycarbonyloxy)succinimide. The resulting N-protected derivative is isolated by column chromatography. The in situ formation of N-protected derivatives is particularly advantageous when isolating derivatives possessing labile 4-N-acyl-containing moiety as the unprotected 4-N-acyl-2-deoxy-3-O-demethylfortimicins are unstable as free bases, but are stable as per-N-protected derivatives or as acid addition salts.

The 2-deoxy-3-O-demethylfortimicin B free base, prepared as above, is reacted with N-(benzyloxycarbonyloxy)-succinimide to prepare 1,2',6'-tri-N-benzyloxycarbonyl-2-deoxy-3-O-demethylfortimicin B according to the prodecures disclosed in U.S. Pat. No. 4,091,032, issued May 23, 1978. The product of the above reaction is isolated by conventional chromatography methods and 4-N-acylated with suitable N-protected amino acids as taught in the above referred to U.S. Pat. No. 4,091,032. For the purposes of this discussion, the term acyl refers to the groups of the particular acid having the hydroxy radical cleaved which are embraced by the various acyl-containing terms for formula I. However, for purposes of the claims, the definition set forth on page 3 supra governs. The benzyloxycarbonyl-4-N-acyl-2-deoxy-3-O-demethylfortimicins, prepared as described above, can be conveniently reduced to the corresponding 4-N-alkyl derivatives with diborane.

After isolation with column chromatography, the benzyloxycarbonyl groups of both the 4-N-acyl and 4-N-alkyl derivatives are conveniently removed by catalytic hydrogenolysis and the products may be isolated as the salts, i.e. the hydrochloride salts in accordance with the procedure detailed in U.S. Pat. No. 4,091,032.

The following examples further illustrate the present invention.

EXAMPLE 1

1,2',6'-Tri-N-benzyloxycarbonylfortimicin B

To a stirred solution of 2.0 g of fortimicin B, 30 ml of water and 60 ml of methanol, cooled in an ice bath, is added 4.44 g of N-(benzyloxycarbonyloxy)succinimide. Stirring is continued at 0° C. for 3 hours and then at room temperature for 22 hours. The major portion of the methanol is evaporated under reduced pressure and the residue is shaken with a mixture of chloroform and water. The chloroform solution is washed with water and dried over anhydrous magnesium sulfate. The chloroform is evaporated and the residue is chromatographed on silica gel. Elution with a solvent system composed of chloroform-methanol-concentrated ammonium hydroxide [23.4:1.4:0.1(v/v/v) yields 1.05 g of product.$[\alpha]_D^{25}+16.5°$(c 1.0,CH$_3$OH); IR(CDCl$_3$) 1712 and 1507 cm$^{-1}$; NMR(CDCl$_3$)δ 1.03(C$_{6'}$—CH$_3$,J$_{6',7'}$=6.0 Hz),2.32(C$_4$—NCH$_3$),3.4-1(OCH$_3$).

EXAMPLE 2

1,2',6'-Tri-N-benzyloxycarbonyl-4,5-salicylaldehyde oxazolidine fortimicin B

A solution of 22 g of 1.2',6'-tri-N-benzyloxycarbonyl-fortimicin B in 396 ml of methanol is treated with 3.96 ml of salicylaldehyde and refluxed for 1 hour. Evaporation of the reaction mixture under reduced pressure gives 26 g of 1,2',6'-tri-N-benzyloxycarbonyl-4,5-salicylaldehyde oxazolidine fortimicin B as a brownish yellow solid: NMR(CDCl$_3$)δ0.94(C$_{6'}$—CH$_3$,J$_{6',7'}$=7.0 Hz),2.34(C$_4$—NCH$_3$),3.49(C$_3$—OCH$_3$),7.31(Cbz).

EXAMPLE 3

1,2',6'-Tri-N-benzyloxycarbonyl-4,5-(2-O-methanesulfonylsalicylaldehyde)-oxazolidine-2-O-methanesulfonylfortimicin B A stirring solution of 26 g of the compound of Example 2 in 154 ml of dry pyridine is treated with 12.26 ml of freshly distilled methanesulfonylchloride. After stirring for 20 hours, the reaction mixture is poured into 2000 ml of 5% sodium hydrogen carbonate and then twice with 1000 ml portions of water. The chloroform is evaporated under reduced pressure and the pyridine is removed by repeated co-distillation with benzene to yield 31.2 g of the desired product: NMR(CDCl$_3$) δ 1.0(C$_{6'}$—CH$_3$,J$_{6',7'}$=7.0 Hz),2.19(C$_4$—NCH$_3$),2.94(-C$_2$—OSO$_2$CH$_3$),3.15(Ar—OSO$_2$CH$_3$),3.60(-C$_3$—OCH$_3$),7.33(Cbz).

EXAMPLE 4

1,2',6'-Tri-N-benzyloxycarbonyl-2-O-methanesulfonylfortimcin B

A stirring solution of 31.2 g of the compound of Example 3 in 1000 ml of tetrahydrofuran is treated with 262 ml of 0.4 N hydrochloric acid. After stirring for 4 hours, the reaction mixture is poured into 5700 ml of 6 N ammonium hydroxide solution and extracted 2 times with 1400 ml portions of chloroform. The combined chloroform extract is washed with 5700 ml of 7% sodium hydrogen sulfite solution and then 2 times with 1180 ml portions of water. Removal of the chloroform under reduced pressure gives 27.35 g of crude 1,2',6'-tri-N-benzyloxycarbonyl-2-O-methanesulfonylfortimicin B. The crude material is chromatographed on a column (6.0×80 cm) of Sephadex LH-20 gel prepared and eluted with 95% ethanol. Fractions containing the desired material are combined and concentrated to dryness under reduced pressure to yield pure product as a glass: $[\alpha]_D^{23}$ +18.5(c 1.0,CH$_3$OH)-;IR(CDCl$_3$)3436,3350,1703,1502,1354 and 1173 cm$^{-1}$; NMR(CDCl$_3$) δ1.07(C$_{6'}$—CH$_3$,J$_{6',7'}$=7.0 Hz),2.34(C$_4$—NCH$_3$),2.87(OSO$_2$CH$_3$),3.48(OCH$_3$).

EXAMPLE 5

2-O-Methanesulfonylfortimicin B tetrahydrochloride

A solution of 4.42 g of the compound of Example 4 in 310 ml of 0.2 N hydrochloric acid in methanol is treated for 4 hours with 4.5 g of 5% palladium on carbon under hydrogen and 3 atmospheres of pressure. The catalyst is filtered off and washed with ethanol. The filtrate is concentrated to dryness under reduced pressure and the excess hydrochloric acid is removed by repeated co-distillation with methanol to leave 2.79 g of product as a white glass: $[\alpha]_D^{25}+91.7°$(c 1.01,$CH_3OH$);IR(KBr)3400,2920,1590,1330 and 1165 $cm^{-1}$.

EXAMPLE 6

1,2-Epiminofortimicin B

A solution prepared from 2.8 g of 2-O-methanesulfonylfortimicin B tetrahydrochloride in 20 ml of water is passed through a column (2.2×20 cm) of an anion exchange resin quaternary ammonium styrene type, e.g., $AG^R$ 2-X, 50–100 mesh resin ($OH^-$ form) sold by Bio-Rad Laboratories, sufficient to remove the chloride ion. Basic elutes are combined and allowed to stand at room temperature for 72 hours. Evaporation of the water under reduced pressure leaves 3.0 g of product. NMR($D_2O$) δ 1.55($C_{6'}$—$CH_3$,$J_{6',7'}=7.0$ Hz),2.83($C_4$—$NCH_3$),4.02(-$C_3$—$OCH_3$),5.42($C_{1'}$,H,J=3.0 Hz).

EXAMPLE 7

2-Deoxyfortimicin B and 1-deamino-2-deoxy-2-epi-aminofortimicin B

A solution prepared from 3.22 g of 1,2(R)-epiminofortimicin B in 250 ml of wet ethanol is treated for 24 hours with 12 g of Raney nickel under 3 atmospheres of hydrogen. The catalyst is collected on a filter and washed with ethanol. The filtrate is concentrated to dryness under reduced pressure to give 2.90 g of a mixture of 2-deoxyfortimicin B and 1-deamino-2-deoxy-2-epi-aminofortmicin B as a white froth. The mixture is chromatographed on a column (2.9×50 cm) of a cation exchange resin $NH_4+$ form(Bio-Rad 70,100–200 mesh, carboxylic styrene type resin sold by Bio-Rad Laboaratories) and eluted with a gradient of water to 1 N ammonium hydroxide. The first elutes are taken to dryness under reduced pressure to yield 1.347 g of pure 2-deoxyfortimicin B:NMR($D_2O$) δ1.5($C_{6'}$—$CH_3$,$J_{6',7'}=7.0$ Hz),2.82($C_4$—$NCH_3$),3.86(-$C_3$—$OCH_3$),5.48($H_{1'}$,$J_{1',2'}=3.5$ Hz).

EXAMPLE 8

1,2',6'-Tri-N-benzyloxycarbonyl-2-deoxyfortimicin B

A stirring ice-bath cooled solution of 0.843 g of 2-deoxyfortimicin B in 12.6 ml of water and 25.3 ml of methanol is treated with 2.09 g of N-(benzyloxycarbonyloxy)-succinimide. After stirring in the cold for 3 hours and then at room temperature for 20 hours, the major portion of the methanol is evaporated under reduced pressure. After addition of 90 ml of water, the product is extracted with 180 ml of chloroform. The aqueous portion is extracted 2 more times with 60 ml portions of chloroform. The combined chloroform extract is washed with water and dried over anhydrous magnesium sulfate. Evaporation under reduced pressure gives a foam which is chromatographed on a column (2.3×70 cm) of silica gel prepared and eluted with a solvent system consisting of chloroform-methanol-concentrated ammonium hydroxide[23.4:1.4:0.1(v/v/v)]. Fractions containing the desired material are collected and evaporated to dryness under reduced pressure to give 0.936 g of product as a colorless froth: NMR($D_2O$)δ1.12($C_{6'}$,$J_{6',7'}=6.0$ Hz),2.26($C_4$—$NCH_3$),3.29(-$C_3$—$OCH_3$),4.78($C_{1'}$,H,J=4.0 Hz),7.31(Cbz).

EXAMPLE 9

Tetra-N-benzyloxycarbonyl-2-deoxyfortimicin A

A stirring solution of 0.807 g of the above material in 14 ml of dry tetrahydrofuran is treated for 18 hours with 0.439 g of the N-hydroxysuccinimide ester of N-benzyloxycarbonylglycine. The tetrahydrofuran is evaporated under reduced pressure to give 1.231 g of colorless froth. The froth is chromatographed on a column (2.0×44 cm) of silica gel prepared and eluted with a solvent system consisting of benzene-methanol-95% ethanol-concentrated ammonium hydroxide[23.5:1.5:1.9:0.2(v/v/v/v)]. Fractions containing tetra-N-benzyloxycarbonyl-2-deoxyfortimicin A are taken to dryness under reduced pressure and rechromatographed on a column of Sephadex LH-20 prepared and eluted with 95% ethanol. Elutes containing the major product are evaporated to dryness to yield 0.623 g of the desired product: NMR($CDCl_3$) δ 1.17($C_{6'}$—$CH_3$),2.86($C_4$—$NCH_3$),3.26(-$C_3$—$OCH_3$),4.83($C_{1'}$,H,J=4.0 Hz),7.30(Cbz).

EXAMPLE 10

2-Deoxyfortimicin A tetrahydrochloride

A solution of 0.463 g of tetra-N-benzyloxycarbonyl-2-deoxyfortimicin A in 60 ml of 0.2 N hydrochloric acid in methanol is treated for 4 hours with 0.463 g of 5% palladium on carbon under 3 atmospheres of hydrogen. The catalyst is collected on a filter and washed with several small portions of methanol. The filtrate is evaporated to dryness under reduced pressure to give a white solid. Excess hydrochloric acid is removed by repeated co-distillation with methanol to leave 0.305 g of 2-deoxyfortimicin A tetrahydrochloride: NMRδ($D_2O$) 1.79($C_{6'}$—$CH_3$,J=7.0 Hz),3.58($C_4$—$NCH_3$),3.90(-$C_3$—$OCH_3$),5.82($C_{1'}$,H,J=4.0 Hz).

EXAMPLE 11

1,2',6',2''-Tetra-N-benzyloxycarbonyl-2-deoxy-3-O-demethylfortimicin A

An aqueous solution, prepared from 0.293 g of 2-deoxyfortimicin A tetrahydrochloride is passed through a column of an anion exchange resin (AG 2×8,50–100 mesh,$OH^-$ form, manufactured by BioRad Laboratories) sufficient to remove the chloride ion. Basic elutes are collected and lyophilized to give 0.205 g of 2-deoxyfortimicin A free base. The freshly prepared 2-deoxyfortimicin A free base is immediately added to 10.3 ml of methylene chloride previously dried over molecular sieves (Linde Type 4A manufactured by Union Carbide Corporation). The 2-deoxyfortimicin A-methylene chloride solution is treated with additional molecular sieve pellets and allowed to stand at room temperature for 18 hours. The pellets are removed and the solution is treated with 0.53 ml of boron tribromide. Stirring is continued in the cold for 0.5 hours and then at room temperature for 22 hours. The solvent is evaporated under reduced pressure and the residue is repeatedly co-distilled with methanol. An aqueous solution of the residue is passed through a column of AG 2×8,50–100 mesh ($OH^-$ form) ion exchange resin. Basic elutes are collected and taken to dryness to give a solid. A stirring ice bath cooled solution prepared from the solid, 4.3 ml of water and 8.6 ml of methanol is treated with 0.526 g of N-(benzyloxycarbonyloxy)-succinimide. Stirring is continued in the cold for 3 hours and then at room temperature for 20 hours. Solvent is evaporated under reduced pressure to leave an oil which is shaken with a mixture of chloroform and water. The chloroform layer is separated and dried over magnesium sulfate to give 0.420 g of solid which is chromatographed on a column (1.9×65 cm) of silica gel prepared and eluted with a solvent system consisting of ethyl acetate-hexane (98:2 v/v). Fractions containing the major component are taken to dryness to yield 0.121 g of 1,2',6',2"-tetra-N-benzyloxycarbonyl-2-deoxy-3-O-demethylfortimicin A: IR(CDCl₃) 3605,3425, 088,3065,3032,2495,1705,1636,1500,1452,1402,1306,121-6,1165,1100,1040 and 1013 cm⁻¹; PMR(CDCl₃)δ 1.16(unresolved d,C₆'—CH₃),2.91(s, C₄—NCH₃)

EXAMPLE 12

2-Deoxy-3-O-demethylfortimicin B tetrahydrochloride

A stirring, ice bath cooled solution is prepared from 0.5 g of 2-deoxyfortimicin B in 25 ml of methylene chloride dried over Linde Type A molecular sieves (Union Carbide Corp.) is treated with 1.3 ml of boron tribromide. The reaction mixture is allowed to stir in the cold for 0.5 hours and then at room temperature for 18 hours. The solvent is removed under reduced pressure and the residue is repeatedly codistilled with methanol to give a solid which is chromatographed on a column (1.2×72 cm) of silica gel prepared and eluted with a solvent system consisting of methylene chloride-methanol-concentrated ammonium hydroxide (1:2:1 v/v/v). Fractions containing the major components are concentrated to dryness under reduced pressure to give 1.02 g of a mixture of 2-deoxy-3-O-demethylfortimicin B, 2-deoxy-3-O-demethylfortamine and starting material.

The mixture obtained from two preparations (1.85 g), prepared as above, is rechromatographed on a column (1.8×28 cm) of cation exchange resin (Bio Rex 70,100–200 mesh,NH₄+ form, manufactured by Bio Rad Laboratories). Elution with a gradient of water to 1 N ammonium hydroxide gives fractions containing only 2-deoxy-3-O-demethylfortimicin B. The fractions are taken to dryness under reduce pressure and the residue is treated with 20 ml of 0.2 N-hydrochloric acid in methanol. Evaporation of the solvent under reduced pressure and repeated co-distillation with methanol gave 0.223 g of 2-deoxy-3-O-demethylfortimicin B isolated as the tetrahydrochloride salt: IR(KBr) 3400,2930,2000,1595,1490,1387,1245,1205,1162,1100,10-32,980,932,899,865,750; PMR(D₂O)δ 1.84(d,C₆'—CH₃,J₆',₇'=7.0 Hz),3.32(s,C₄—NCH₃),5.91 (d,H₁',J₁',₂'=4.0 Hz).

EXAMPLE 13

1,2',6'-Tri-N-benzyloxycarbonyl-2-deoxy-3-O-demethylfortimicin B

A stirring, ice-bath cooled solution, prepared from 0.163 g of 2-deoxy-3-O-demethylfortimicin B in 25 ml of water and 5.0 ml of methanol, is treated with 0.389 g of N-(benzyloxycarbonyloxy)succinimide. Stirring is continued in the cold for 3 hours and then at room temperature for 18 hours. Solvent is removed under reduced pressure to leave a syrup which is dissolved in chloroform. After washing with water, the chloroform solution is dried over magnesium sulfate and taken to dryness to give 0.309 g of residue. The residue is chromatographed on a column (1.4×70 cm) of silica gel prepared and eluted with a solvent system consisting of methylene chloride-methanol-concentrated ammonium hydroxide (23.4:1.9:0.1 v/v/v). Fractions containing only the major component are taken to dryness to give 0.184 g of 1,2',6'-tri-N-benzyloxcarbonyl-2-deoxy-3-O-demethylfortimicin B:IR(CDCl₃)3433,3330,3087,3063,3032,2947,1705,1650-,1600,1583,1504,1452,1400,1307,1219,1033,1020 cm⁻¹ PMR(CDCl₃)δ 1.14(d,C₆'—CH₃,J₆',₇'=6.5 Hz),2.34(s,C₄—NCH₃).

EXAMPLE 14

1,2',6',2"-Tetra-N-benzyloxycarbonyl-2-deoxy-3-O-demethylfortimicin A

A stirring solution prepared from 0.114 g of 1,2',6'-tri-N-benzyloxycarbonyl-2-deoxy-3-O-demethylfortimicin B in 3.6 ml of tetrahydrofuran is treated with 0.053 g of the N-hydroxysuccinimide ester of benzyloxycarbonylglycine. Stirring is continued at room temperature for 22 hours. The tetrahydrofuran is evaporated under reduced pressure to leave a colorless residue. The product is purified by chromatography on a column (1.6×70 cm) of silica gel using ethyl acetate-ethanol(98:2 v/v) as the eluent to give 0.183 g of 1,2',6',2"-tetra-N-benzyloxcarbonyl-2-deoxy-3-O-demethylfortimicin A identical in all respects with the material prepared in Example 11.

EXAMPLE 15

1,2',6',3"-Tetra-N-benzyloxycarbonyl-4-N-sarcosyl-2-deoxy-3-O-demethylfortimicin B A stirring solution prepared from 0.150 g of 1,2',6'-tri-N-benzyloxycarbonyl-2-deoxy-3-O-demethylfortimicin B, 0.057 g of N-benzyloxysarcosine, 0.065 g of 1-hydroxybenzotriazole and 1.5 ml of tetrahydrofuran is treated with 0.054 g of N,N-dicyclohexylcarbodiimide in 1.5 ml of tetrahydrofuran. Stirring is continued for 20 hours at room temperature. Insoluble dicyclohexylurea is removed by filtration and the filtrate evaporated to dryness to leave a residue. The residue is chromatographed on a column of silica gel using benzene-methanol-95% ethanol-concentrated ammonium hydroxide [23.5:1.4:2.0:0.2 (v/v/v/v)] as the eluent. Fractions containing only the major component are taken to dryness to give 1,2',6',2"-tetra-N-benzyloxycarbonyl-4-N-sarcosyl-2-deoxy-3-O-demethylfortimicin B.

EXAMPLE 16

1,2',6',3"-Tetra-N-benzyloxycarbonyl-4-N-β-alanyl-2-deoxy-3-O-demethylfortimicin B A stirring solution prepared from 0.045 g of 1,2',6'-tri-N-benzyloxycarbonyl-2-deoxy-3-O-demthylfortimicin B in 2 ml of tetrahydrofuran is treated with 0.029 g of N-hydroxy-5-norbornene-2,3-dicarboximidyl-N-benzyloxycarbonyl-β-alanine. Stirring is continued for 20 hours at room temperature. The solvent is evaporated to leave a residue which is chromatographed on a column of silica gel using dichloroethane-95% ethanol-concentrated ammonium hydroxide (20:20:0.4 v/v/v) as the eluent to give 1,2',6',2"-tetra-N-benzyloxycarbonyl-4-N-β-alanyl-2-deoxy-3-O-demethylfortimicin B.

EXAMPLE 17

1,2',6',2"-Tetra-N-benzyloxycarbonyl-4-N-(β-aminoethyl)-2-deoxy-3-O-demethylfortimicin B To a stirring nitrogen purged solution prepared from 0.40 g of 1,2',6',2"-tetra-N-benzyloxycarbonyl-2-deoxy- 3-O-demethylfortimicin A and 6.0 ml of dry tetrahydrofuran is added 1.25 ml of a 1 M solution of diborane in tetrahydrofuran. Stirring is continued for 3 hours under a nitrogen atmosphere and then an additional 1.0 ml of the diborane solution is added. After stirring for another 2.5 hours, the excess diborane is consumed by the addition of water. The solution is evaporated under reduced pressure and the residue is repeatedly co-distilled with methanol. The resulting solid is chromatographed on a column of (1.2×60 cm) of silica gel using a solvent system composed of benzene-methanol-95% ethanol-concentrated ammonium hydroxide (23.5:1.5:1.9:0.2 v/v/v/v) to give 1,2',6',2''-tetra-N-benzyloxycarbonyl-4-N-($\beta$-aminoethyl)-2-deoxy-3-O-demethylfortimicin B.

EXAMPLE 18

2-Deoxy-3-O-Demethylfortimicin A tetrahydrochloride

A solution prepared from 0.084 g of 1,2',6',2''-tetra-N-benzyloxycarbonyl-2-deoxy-3-O-demethylfortimicin A and 8.0 ml of 0.2 N hydrochloric acid in methanol is hydrogenated over 0.09 g of 5% palladium on carbon for 4 hours under 3 atmospheres of hydrogen. The catalyst is collected on a filter and washed with methanol. The filtrate is concentrated to dryness and the excess hydrochloric acid is removed by repeated co-distillation with methanol under reduced pressure to give 0.053 g of 2-deoxy-3-O-demethylfortimicin A tetrahydrochloride:IR(KBr)3400,2910,1640,1600,1487,1400,1330,1100,1035,980,903,753 cm$^{-1}$;PMR(D$_2$O)$\delta$ 1.80(d,C$_{6'}$—CH$_3$,J$_{6',7'}$=7.0 Hz);3.62(s,C$_4$—NCH$_3$),5.81(d,H$_{1'}$,J$_{1',2'}$=3.5 Hz).

EXAMPLE 19

4-N-Sarcosyl-2-deoxy-3-O-demethylfortimicin B tetrahydrochloride

A solution prepared from 0.063 g of 1,2',6',2''-tetra-N-benzyloxycarbonyl-4-N-sarcosyl-2-deoxy-3-O-demethylfortimicin B in 12 ml of 0.2 N hydrochloric acid in methanol is hydrogenated over 0.065 g of 5% palladium on carbon under 3 atmospheres of hydrogen. Work up as described for Example 18 results in 4-N-sarcosyl-2-deoxy-3-O-demethylfortimicin B tetrahydrochloride.

EXAMPLE 20

4-N-$\beta$-Alanyl-2-deoxy-3-O-demethylfortimicin B tetrahydrochloride

A solution prepared from 0.048 g of 1,2',6',3''-tetra-N-benzyloxycarbonyl-4-N-$\beta$-alanyl-2-deoxy-3-O-demethylfortimicin B and 10 ml of 0.2 N hydrochloric acid in methanol is hydrogenated over 0.05 g of 5% palladium on carbon under 3 atmospheres of hydrogen for 4 hours. The catalyst is collected on a filter and washed with methanol and the final product isolated as described in Example 18 to obtain 4-N-$\beta$-alanyl-2-deoxy-3-O-demethylfortimicin B tetrahydrochloride.

EXAMPLE 21

4-N-($\beta$-Aminoethyl)-2-deoxy-3-O-demethylfortimicin B pentahydrochloride

A solution of 0.058 g of 1,2',6',2''-tetra-N-benzyloxycarbonyl-4-N-($\beta$-aminoethyl)-2-deoxy-3-O-demethylfortimicin B in 6 ml of 0.2 N hydrochloride acid is hydrogenated over 0.06 g of 5% palladium on carbon under 3 atmospheres of hydrogen for 4 hours. The pentahydrochloride was obtained following the method of Example 18.

EXAMPLE 22

In Vitro Antibiotic Activity of 2-Deoxy-3-O-demethylfortimicin A tetrahydrochloride The in vitro antibiotic activities of fortimicin A tetrahydrochloride, 2-deoxy-fortimicin A tetrahydrochloride, 3-O-demethylfortimicin A tetrahydrochloride and 2-deoxy-3-O-demethylfortimicin A tetrahydrochloride are set forth in Table I.

The in vitro antibiotic activities are determined by a two-fold agar dilution method using Mueller-Hinton agar, 10 ml per Petri dish. The agar is inoculated with one loopful (0.001 ml loop) of a 1:10 dilution of a 24 hour broth culture of the indicated test organism and incubated at 37° C. for 24 hours. Appropriate fortimicins are used as control antibiotics. The activities, listed in the following Table I, minimum inhibitory concentrations(MIC) are expressed in mcg/ml.

TABLE I

| | Minimum Inhibitory Concentration (mcg of base/ml) | | | |
|---|---|---|---|---|
| Organism | Fortimicin A . 4HCl | 2-Deoxyfortimicin A . 4 HCl | 3-O-Demethylfortimicin A . 4HCl | 2-Deoxy-3-O-demethylfortimicin A . 4HCl |
| Staphyloccocus aureus Smith | 0.78 | 0.78 | 0.54 | 0.39 |
| Streptoccocus faecalis 10541 | 50 | 50 | 17 | 50 |
| Enterobacter aerogenes 13048 | 3.1 | 3.1 | 2.1 | 3.1 |
| Escherichia coli Juhl | 6.2 | 6.2 | 2.1 | 6.2 |
| Escherichia coli BL 3676(Res) | 25 | 25 | 8.6 | 12.5 |
| Klebsiella pneumoniae 10031 | 3.1 | 1.56 | 1.1 | 3.1 |
| Providencia 1577 | 6.2 | 3.1 | 1.1 | 1.56 |
| Pseudomonas aeruginosa BMH #10 | 0.78 | 0.78 | 0.27 | 0.78 |
| Pseudomonas aeruginosa KY 8512 | 12.5 | 12.5 | 2.1 | 3.1 |
| Pseudomonas aeruginosa KY 8516 | 100 | 50 | 69 | 100 |
| Pseudomonas aeruginosa 209 | 100 | 100 | 69 | 100 |
| Pseudomonas aeruginosa 27853 | 12.5 | 12.5 | — | 6.2 |
| Salmonella typhimurium Ed #9 | 1.56 | 1.56 | 1.1 | 1.56 |
| Serratia marcescens 4003 | 3.1 | 3.1 | 4.3 | 3.1 |
| Shigella sonnei 9290 | 12.5 | 12.5 | 4.3 | 12.5 |
| Proteus vulgaris JJ | 3.1 | 3.1 | 2.1 | 3.1 |
| Proteus mirabilis Fin. #9 | 6.2 | 6.2 | 2.1 | 3.1 |

We claim:

1. A 2-deoxy-3-O-demethylfortimicin A and B and 2-deoxy-3-O-demethyl-4-N-fortimicin B derivatives represented by the formula:

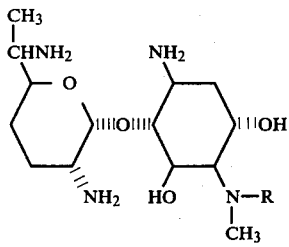

wherein R is selected from the group consisting of hydrogen, acyl, aminoacyl, diaminoacyl, N-mono loweralkylaminoalkyl, N,N-diloweralkylaminoalkyl, hydroxy-substituted aminoacyl, loweralkyl, aminoloweralkyl, N-monoloweralkylaminoloweralkyl, N,N-diloweralkylaminoloweralkyl and hydroxy-substituted aminoloweralkyl and the pharmaceutically acceptable salts thereof.

2. A compound of claim 1 wherein R is hydrogen:2-deoxy 3-O-demethyl-fortimicin B or a pharmaceutically acceptable salt thereof.

3. A compound of claim 1 wherein R is acyl.

4. A compound of claim 3 wherein R is aminoacyl.

5. A compound of claim 4 wherein R is glycyl: 2-deoxy-3-O-demethylfortimicin A or a pharmaceutically acceptable salt thereof.

6. A compound of claim 5: 2-deoxy-3-O-demethylfortimicin A tetrahydrochloride.

7. A compound of claim 5: 2-deoxy-3-O-demethylfortimicin A disulfate.

8. A compound of claim 1 wherein R is 2-deoxy-3-O-demethyl-4-N-sarcosylfortimicin B or a pharmaceutically acceptable salt thereof.

9. A compound of claim 8: 2-deoxy-3-O-demethyl-4-N-sarcosylfortimicin B tetrahydrochloride.

10. A compound of claim 1 wherein R is 2-deoxy-3-O-demethyl-4-N-β-alanylfortimicin B or a pharmaceutically acceptable salt thereof.

11. A compound of claim 10: 2-deoxy-3-O-demethyl-4-N-β-alanylfortimicin B tetrahydrochloride.

12. A compound of claim 1 where in R is aminoalkyl: 2-deoxy-3-O-demethyl 4-N-(β-aminoethyl)fortimicin B or a pharmaceutically acceptable salt thereof.

13. A compound of claim 12: 2-deoxy-3-O-demethyl-4-N-(β-aminoethyl)fortimicin B pentahydrochloride.

14. A pharmaceutical antibiotic composition comprising a therapeutically effective amount of a compound of claim 1 and a pharmaceutically acceptable carrier or diluent.

15. A composition of claim 14 wherein said compound is 2-deoxy-3-O-demethylfortimicin A or a pharmaceitically acceptable salt thereof.

16. A composition of claim 14 wherein said compound is 2-deoxy-3-O-demethyl-4-N-sarcosylfortimicin B or a pharmaceutically acceptable salt thereof.

17. A composition of claim 14 wherein said compound is 2-deoxy-3-O-demethyl-4-N-β-alanylfortimicin B or a pharmaceutically acceptable salt thereof.

18. A composition of claim 14 wherein said compound is 2-deoxy-3-O-demethyl-4-N-(β-aminoethyl)fortimicin B or pharmaceutically acceptable salt thereof.

19. A method of treating a patient suffering from an infection caused by a susceptible organism comprising administering a therapeutically effective amount of a compound of claim 1 to said patient.

* * * * *